United States Patent
Ching et al.

(10) Patent No.: US 8,043,991 B2
(45) Date of Patent: Oct. 25, 2011

(54) SELECTIVE ISOMERIZATION OF OLEFINS TO ALKENES USING A MESOPOROUS CATALYST

(75) Inventors: Ta Yen Ching, Houston, TX (US); Jeffery Gee, Kingwood, TX (US); Ruthann M. Hickox, Spring, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 47 days.

(21) Appl. No.: 12/639,729

(22) Filed: Dec. 16, 2009

(65) Prior Publication Data

US 2010/0093521 A1    Apr. 15, 2010

Related U.S. Application Data

(62) Division of application No. 11/383,660, filed on May 16, 2006, now Pat. No. 7,655,827.

(51) Int. Cl.
  *B01J 31/02* (2006.01)
(52) U.S. Cl. ....................................................... 502/158
(58) Field of Classification Search ........................ None
  See application file for complete search history.

(56) References Cited

U.S. PATENT DOCUMENTS

| | | | |
|---|---|---|---|
| 6,403,853 B1 | 6/2002 | Abrevaya et al. | |
| 6,906,208 B2 | 6/2005 | Shan et al. | |
| 6,911,506 B2 | 6/2005 | Small et al. | |
| 6,960,551 B2 | 11/2005 | Ozin et al. | |
| 7,001,964 B2 | 2/2006 | Small | |
| 7,122,688 B2 * | 10/2006 | Lin et al. | 554/169 |
| 2004/0072674 A1 * | 4/2004 | Ozin et al. | 502/60 |
| 2007/0287875 A1 | 12/2007 | Ching et al. | |

OTHER PUBLICATIONS

Inagaki et al, novel ordered mesoporous materials with hybrid organic-inorganic network in the frameworks, 2000, studies in durface science and catalysis, 129.*
Prins et al, metal phosphides and zeolite-like mesoporous materials as catalysts, 2001, chimia, 55, No. 10.*
Beck, J.S., et al., "A New Family of Mesoporous Molecular Sieves Prepared with Liquid Crystal Templates," J. Am. Chem Soc., 1992, vol. 114, pp. 10834-10843, American Chemical Society.

* cited by examiner

*Primary Examiner* — Melvin Mayes
*Assistant Examiner* — Stefanie Cohen
(74) *Attorney, Agent, or Firm* — Conley Rose, P.C.; Rodney B. Carroll; Lynda S. Jolly

(57) ABSTRACT

A process for selectively making 2-alkenes from a NAO using a mesoporous catalyst that has been surface modified with a Brönsted acid compound. The Brönsted acid compound has a reactive silane connector, an organic linking group, and a Brönsted acid group. The mesoporous catalyst has an average pore diameter in a range of about 12 to about 100 Angstroms and a surface area of between about 400 to about 1400 $m^2$/gram.

20 Claims, No Drawings

SELECTIVE ISOMERIZATION OF OLEFINS TO ALKENES USING A MESOPOROUS CATALYST

CROSS-REFERENCE TO RELATED APPLICATION

This is a Divisional Application of U.S. patent application Ser. No. 11/383,660, filed May 16, 2006 and published as U.S. 2007/0287875A1, now U.S. Pat. No. 7,655,827 and entitled "Selective Isomerization of Olefins to Alkenes Using a Mesoporous Catalyst," which is hereby incorporated by reference herein in its entirety.

TECHNICAL FIELD OF THE INVENTION

The present invention relates generally to mesoporous catalysts used to isomerize normal alpha olefins.

BACKGROUND OF THE INVENTION

Olefins, especially those containing about 6 to about 20 carbon atoms, are important items of commerce. Olefins are used as intermediates in the manufacture of detergents, synthetic lubricants, lube oil additives, plasticizers, and surfactants. Olefins are also used as monomers, such as in linear low-density polyethylene, high-density polyethylene, polypropylene, polystyrene, etc. and as intermediates for many other types of products. As a consequence, improved methods of making these compounds are of value.

Most commercially produced olefins are made by the oligomerization of ethylene, catalyzed by various types of compounds, such as alkylaluminum compounds, certain nickel-phosphine complexes, and a titanium halide with a Lewis acid such as diethylaluminum chloride (DEAC). In many of these processes, significant amounts of branched and/or internal olefins and/or diolefins are also produced. Because the location of the double bond in olefins affects the physical properties of the olefins produced, generally, branched and/or internal olefins and/or diolefins perform differently from terminal olefins, i.e. normal alpha olefins (NAOs). The position of the double bond in the olefins also has a significant impact on the physical properties of derivatives made from the olefins. For example, a sulfonate salt prepared from a terminal olefin often functions as an oil-in-water surfactant, but a sulfonate salt prepared from an internal olefin, such as in the middle of the molecule, forms a double tail surfactant that performs well as a surfactant in inverted water-in-oil emulsions.

When a terminal olefin is isomerized, the double bond migrates to an internal position to form a more thermodynamically favored isomer. Under normal circumstances, the double bond migration will lead to a thermodynamic statistical distribution of the double bond at each carbon position of the molecule chain.

Because thermodynamics control double bond distribution during known olefin isomerization processes, economically producing an olefin with predominately 2-alkenes has been difficult, particularly when using heterogeneous catalysts. Attempts have been made to selectively produce 2-alkenes using homogeneous catalysts. Homogeneous catalysts, however, are generally more expensive than heterogeneous catalysts. A need exists for an economical process to selectively produce 2-alkenes. It would be advantageous if the process used heterogeneous catalysts.

SUMMARY OF THE INVENTION

In view of the foregoing, the present invention provides processes for selectively isomerizing normal alpha olefins (NAO) to produce 2-alkenes using a mesoporous catalyst that has had its surface modified with a substance or composition that contains a Brönsted acid compound. The mesoporous catalyst has mesoporous pore diameters that allow the NAO and products of varying sizes to enter and exit the catalyst. The Brönsted acid compound generally has three components, namely a reactive silane connector, an organic linking group, and a Brönsted acid group. The reactive silane connector contains a silicon atom and at least one leaving group attached to the silicon atom that connects the Brönsted acid compound to a mesoporous silicate. The reactive silane connector can be a halosilane group, an alkoxysilane group, or combinations thereof. The organic linking group can be aromatic group, a fluoroaromatic group, an alkylene group, a fluoroalkylene group, a poly(etherfluoroalkyl) group, or combinations thereof. The Brönsted acid group can be a sulfonic acid group, a carboxylic acid group, or combinations thereof.

Once the surface of the mesoporous silicate has been modified, the mesoporous catalyst forms and minimally has a general structure as follows:

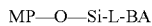

wherein MP is a mesoporous silicate, L is the organic linking group, and BA is the Brönsted acid group. The mesoporous silicate contains silica and optionally aluminate silicate.

The mesoporous catalyst has an average pore diameter ranging from about 12 Angstroms (Å) (1.2 nanometers) to about 100 Å (10 nanometers), a surface area ranging from about 400 $m^2/g$ to about 1400 $m^2/g$, and a pore volume ranging from about 0.5 cc/g to about 2.0 cc/g. The properties of the mesoporous catalyst do not change substantially between pre- and post-surface modification of the mesoporous silicate.

The processes described herein can be performed in the presence of an optional mobile phase acid. The mobile phase acid is not required, but can be used.

In addition to the processes described herein, the present invention also provides the mesoporous catalyst that has been surface modified with the Brönsted acid compound as an embodiment of the present invention. The mesoporous catalyst has an average diameter ranging from about 12 Å to about 100 Å.

DETAILED DESCRIPTION OF THE INVENTION

A process for selectively making a 2-alkene is provided as an embodiment of the present invention. In this embodiment, a NAO having at least 6 carbon atoms is contacted with a mesoporous catalyst. The mesoporous catalyst has been surface modified with a substance or composition comprising a Brönsted acid compound. The NAO is isomerized in a reactor to produce a reactor effluent comprising the 2-alkene. In an aspect, the reactor effluent comprises less than about 8 wt. % olefin dimer and no added branched olefins other than those contained within the feed stream. The reactor effluent contains at least 35 wt. % 2-alkene. In some embodiments, the reactor effluent can comprise at least 50 wt. % 2-alkene.

The substance containing the Brönsted acid compound generally comprises a reactive silane connector, an organic linking group, and a Brönsted acid group. Each component of the Brönsted acid compound is described herein. Each Brönsted acid compound component described herein is an independent element. The quantity or number of each component present in the Brönsted acid compound can be independent of the quantity of other components present in the Brönsted acid compound. Other independent properties that are described herein can be used to further describe the Brönsted acid compound.

Once the surface of the mesoporous silicate has been modified, the mesoporous catalyst is formed that minimally has a general structure as follows:

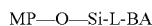

MP—O—Si-L-BA wherein MP comprises a mesoporous silicate, L is the organic linking group, and BA is the Brönsted acid group. One skilled in the art will recognize that the silicon atom in the above structure has two undesignated valencies. As used herein, the undesignated silicon valencies can each independently be a MP—O— linkage, a linking group having the Brönsted acid group, any other group attached to the silicon atom from the Brönsted acid compound comprising a reactive silane connector (e.g. an organic group, a hydrocarbon group, X, R'O—, or a hydroxy group). The mesoporous silicate comprises silica and optionally aluminate silicate. The organic linking group L can be a hydrocarbon group. Alternatively, L can be aromatic group, a fluoroaromatic group, an alkylene group, a fluoroalkylene group, a poly(etherfluoroalkyl) group, or combinations thereof.

The Brönsted acid compound used to surface modify the mesoporous silicate can include a chemically bonded strong Brönsted acid group. Various methods of modifying the surface of the mesoporous silicate can be used in embodiments of the present invention. One way of modifying the surface of the mesoporous silicate is by adding a phenyl group having a reactive siloxy group, such as phenyl alkoxysilane or phenyl trichlorosilane, to the mesoporous silicate in a solvent and allowing hydrolysis and condensation of the siloxy group to occur, followed by the addition of a sulfonic acid group on the phenyl linkage to produce the mesoporous catalyst. Alternatively, a vinyl group having a reactive siloxy group, such as vinyl alkoxysilane or vinyl trichlorosilane, can be first introduced or added to the mesoporous silicate in a solution, followed by sulfonation to provide the mesoporous catalyst having a structure MP—O—Si—CH$_2$—CH$_2$—SO$_3$H or MP—O—Si—CH(CH$_3$)—SO$_3$H. Another way of preparing the surface of the mesoporous silicate is by adding a compound having the structure (R'O)$_3$—Si—R—BA to the mesoporous silicate; or alternatively adding a compound having the structure (R'O)$_3$—Si—R—CO$_2$Na or (R'O)$_3$—Si—R—SO$_3$Na to the mesoporous silicate followed by acidifying the modified surface of the mesoporous silicate to produce the mesoporous catalyst having the structure MP—O—Si—R—CO$_2$H or MP—O—Si—R—SO$_3$H. In an embodiment, R can be an alkylene, fluoroalkylene, poly(alkylene ether), poly (fluoroalkylene ether), arylene, or fluoroarylene hydrocarbon connecting linkages. Yet another way of preparing the surface of the mesoporous silicate is by adding a compound having the following structure to the mesoporous silicate: (R'O)$_3$Si—CF$_2$—CF$_2$—CO$_2$Na or (R'O)$_3$Si—CF$_2$—CF$_2$—SO$_3$Na, followed by acidifying the compound to produce the mesoporous catalyst having the structure MP—O—Si—CF$_2$—CF$_2$—CO$_2$H or MP—O—Si—CF$_2$—CF$_2$—SO$_3$H. In some embodiments, R' comprises a hydroxy group. In some embodiments, R' is CH$_3$, C$_2$H$_5$, or C$_3$H$_7$.

In some embodiments, the mesoporous silicate has its surface modified by a surface preparation method that includes adding a substance having a Brönsted acid compound or alternatively, a compound that is capable of being converted to a Brönsted acid compound. In some embodiments, the mesoporous silicate has its surface modified by a surface preparation method selected from the group consisting of phenylsulfonation; addition of triethoxy silyl gamma propyl mercaptan followed by oxidation into sulfonic acid; and addition of a silane of a fluoroalkylene hydrocarboxylate salt, a fluoroarylene carboxylate salt, a fluoroalkylene sulfonate salt, or a fluoroarylene sulfonate salt, followed by acidifying the salt back to its acid equivalents. Oxidation can be performed using peroxide or other methods apparent to those of skill in the art. Other suitable means for modifying the surface of the mesoporous silicate to produce the mesoporous catalyst can be used, will be apparent to those of ordinary skill in the art, and are to be considered within the scope of the present invention.

Once the surface of the mesoporous silicate has been modified by the addition of the Brönsted acid compound, reactive Brönsted acid sites are available for reaction at the surface of the mesoporous catalyst. The reactive Brönsted acid sites are attached to the mesoporous catalyst through a stable —Si—O—Si— linkage between the a silicon atom of the mesoporous silicate and a silicon atom of the Brönsted acid compound. More than one —Si—O—Si— linkage can form, as described herein.

In embodiments of the present invention, numerous process variables can be changed without deviating from the scope of the invention. For example, isomerizing the NAO can be performed at a temperature of up to about 300° C. In some embodiments, the temperature is in a range of about 65° C. to about 300° C.; alternatively, from about 100° C. to about 250° C.; or alternatively, from about 150° C. to about 200° C. In an aspect, the NAO is reacted at a pressure ranging from about atmospheric pressure to about 200 atm. In an aspect, the process can be a batch process or a continuous process. Other process variables can be changed, as will be apparent to those of ordinary skill in the art, and are to be considered within the scope of the present invention.

The NAO can be reacted in the presence of a small amount of a mobile phase acid. Suitable mobile phase acids include propionic acid, methane sulfonic acid, acetic acid, trifluoroacetic acid, toluenesulfonic acid, and combinations thereof. The molar percentage of the mobile acid is about 1 mol. % to about 10 mol. % of the bonded surface acids. In some embodiments, the mobile acid is used in a range of about 2 mol. % to about 5 mol. % to adhere on the surface of the mesoporous catalyst and to improve the activity of the mesoporous catalyst without behaving like a homogeneous acid catalyst. Other suitable mobile phase acids will be apparent to those of ordinary skill in the art and are to be considered within the scope of the present invention. A mobile phase acid is optional, i.e. not required, but can be used.

As another embodiment of the present invention, a process for selectively making a 2-alkene is provided. In this embodiment, a NAO having at least 6 carbon atoms is contacted with a mesoporous catalyst that has had its surface modified with a Brönsted acid compound comprising a reactive silane connector, an organic linking group, and a Brönsted acid group. The NAO can have at least 6 carbon atoms. The NAO can have from 6 to 20 carbon atoms; alternatively, from 8 to 20 carbon atoms; alternatively, from 12 to 20 carbon atoms; or alternatively, from 6 to 10 carbon atoms. The NAO is then reacted at a temperature of up to about 300° C. in a reactor to produce a reactor effluent comprising the 2-alkene. In an aspect, the reactor effluent comprises at least 35 wt. % 2-alkene. In some embodiments, the reactor effluent can comprise at least 50 wt. % 2-alkene. In other embodiments, it is believed that the reactor effluent comprises at least 25 percent more 2-alkene than the thermodynamic statistical distribution of 2-alkene provides; alternatively, at least 35 percent more 2-alkene than the thermodynamic statistical distribution of 2-alkene provides; alternatively, at least 50 percent more than the thermodynamic statistical distribution of 2-alkene provides. With knowledge of the alpha olefin carbon number, one skilled in the art can readily determine the thermodynamic statistical distribution of 2-alkene for a particular alpha olefin or mixture of alpha olefins.

As another embodiment of the present invention, a mesoporous catalyst for isomerizing NAO to a composition comprising at least 35 wt. % 2-alkene and less than 8 wt. % dimers, branched olefins, or combinations thereof is provided. In some embodiments, the mesoporous catalyst isomerizes the NAO to a composition comprising at least 25 percent more 2-alkene than the thermodynamic statistical distribution of 2-alkene provides (or any other amount of 2-alkene described herein) and less than 8 wt. % dimers, branched olefins, or combinations thereof. In other embodiments, the composition comprises greater than about 50 wt. % 2-alkene. In an aspect, the mesoporous catalyst has a surface that has been modified with a Brönsted acid compound to provide reactive acid sites at the surface of the mesoporous catalyst. The mesoporous catalyst has an average pore diameter in a range of about 12 Å to about 100 Å.

In an aspect, the mesoporous silicate has been modified with the Brönsted acid compound to produce the mesoporous catalyst by a surface preparation method selected from the group consisting of phenylsulfonation; addition of triethoxy gamma propyl mercaptan followed by oxidation into sulfonic acid; and addition of a silane of a fluoroalkylenecarboxylate salt, a fluoroarylcarboxylate salt, a fluoroalkylene sulfonate salt, or a fluoroarylsulfonate salt, followed by contact with a strong acid. Oxidation can be performed using peroxide or other methods apparent to those of skill in the art. Other methods of surface modification will be apparent to those of ordinary skill in the art and are to be considered within the scope of the present invention.

The processes described herein are economical and environmentally friendly because the mesoporous catalyst used herein can be easily recycled for continuous usage, and, if needed, the mesoporous catalyst can be rejuvenated. If the reactivity of the surface-modified mesoporous catalyst is reduced, the mesoporous catalyst can be rejuvenated by surface modifying the mesoporous catalyst again using the methods described herein. The rejuvenation replenishes the reactive acid sites located at the surface of the mesoporous catalyst to increase the reactivity of the mesoporous catalyst. Rejuvenation enables the mesoporous catalyst to be used longer, which reduces the amount of new catalyst that needs to be purchased and the amount of spent catalyst that needs to be discarded.

The resulting 2-alkenes produced using the methods and mesoporous catalysts described herein can be used in many types of products. For example, the 2-alkenes can be used for making products or derivatives from oxidation, halogenation, epoxidation, dimerization, and hydroformylation processes. The 2-alkene derivatives can be used in detergents, surfactants, surface activating agents, drilling fluids, lubricants, and the like. Other suitable uses of the 2-alkenes will be apparent to those having ordinary skill in the art and are to be considered within the scope of the present invention.

Pre- and Post-Surface Modified Mesoporous Catalyst

In an aspect, in some embodiments, the mesoporous silicate used to produce the mesoporous catalyst of the present invention is a mesoporous inorganic solid material. The mesoporous silicate comprises silica and can be in either silicate or aluminate silicate forms. The mesoporous silicate can be prepared using methods apparent to those of ordinary skill in the art and are to be considered within the scope of the present invention.

The properties used herein to describe the mesoporous catalyst apply to the pre-surface modification mesoporous silicate and the post-surface modification mesoporous catalyst. The properties do not substantially change during surface modification of the mesoporous silicate to produce the mesoporous catalyst.

The mesoporous silicate and the mesoporous catalyst can have various shapes and sizes. In an aspect, for example, the mesoporous silicate and the mesoporous catalyst have a tubular pore shape.

In an aspect, the mesoporous silicate and the mesoporous catalyst have a pore volume in a range of about 0.5 cc/gram to about 2.0 cc/gram. Alternatively, the pore volume can be in a range of about 0.8 to about 1.5 cc/gram; or alternatively, from about 1.0 to about 1.25 cc/gram.

In some embodiments, the mesoporous silicate and the mesoporous catalyst have an average pore diameter in a range of about 12 Å to about 100 Å; alternatively, from about 15 Å to about 75 Å; or alternatively, from about 20 Å to about 50 Å.

In some embodiments, the mesoporous silicate and the mesoporous catalyst have a surface area of greater than about 400 m$^2$/g. In an aspect, the mesoporous silicate and the mesoporous catalyst have a surface area of between about 400 m$^2$/g to about 1400 m$^2$/g; or alternatively, from about 500 m$^2$/g to about 1100 m$^2$/g.

The mesoporous silicate and the mesoporous catalyst generally have honeycombed shaped pores having substantially uniform diameter. The mesoporous silicate and the mesoporous catalyst have an average diameter in a range of about 15 Å to about 70 Å; alternatively, from about 15 Å to about 60 Å; or alternatively, from about 20 Å to about 50 Å.

Brönsted Acid Compound

The Brönsted acid compounds useful in the present invention generally include strong acids, such as sulfonic acids and fluoroalkylcarboxylic acids. In an aspect, the Brönsted acid compound comprises a reactive silane connector, an organic linking group, and a Brönsted acid group. In some embodiments, the reactive silane connector and the organic linking group can be introduced sequentially. In some embodiments, the organic linking group and the Brönsted acid group can be introduced at the same time in one compound.

In some embodiments, the Brönsted acid compound has a formula as follows:

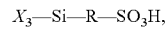

$X_3$—Si—R—SO$_3$H, wherein X comprises a halogen or an alkoxy group and R comprises aromatic group, a fluoroaromatic group, an alkylene group, a fluoroalkylene group, a poly(etherfluoroalkyl) group, or combinations thereof. One skilled in the art will recognize that the silicon atom in the above structure has two undesignated valencies. As used herein, the undesignated silicon valencies can each independently be X, a linking group having a Brönsted acid group, or any other group attached to the silicon atom (e.g. a hydrocarbon group not having a Brönsted acid group). When this type of Brönsted acid compound is used, $X_3$—Si is the reactive silane connector, R is the organic linking group, and SO$_3$H is the Brönsted acid group. X can be Cl, Br, or OR', with R' being CH$_3$, C$_2$H$_5$, or C$_3$H$_7$. R can be —(CH$_2$)$_x$—, —C$_6$H$_4$—, —(CF$_2$—CF$_2$)$_x$—, —(CF$_2$—CF$_2$)$_{x-O-(CF2}$—CF$_2$)$_y$—, or —C$_6$F$_4$—.

In some embodiments, the Brönsted acid compound has a formula as follows:

$X_3$—Si—FR—COOH, wherein X comprises a halogen or an alkoxy group and FR comprises aromatic group, a fluoroaromatic group, an alkylene group, a fluoroalkylene group, a poly(etherfluoroalkyl)

group, or combinations thereof. One skilled in the art will recognize that the silicon atom in the above structure has two undesignated valencies. As used herein, the undesignated silicon valencies can each independently be X, a FR linking group having a Brönsted acid group, or any other group attached to the silicon atom (e.g. a hydrocarbon group not having a Brönsted acid group). When this type of Brönsted acid compound is used, $X_3$—Si is the reactive silane connector, FR is the organic linking group, and COOH is the Brönsted acid group. X can be Cl, Br, or OR', with R' being $CH_3$, $C_2H_5$, or $C_3H_7$. FR can be —$(CH_2)_x$—, —$C_6H_4$—, —$(CF_2$—$CF_2)_x$—, —$(CF_2$—$CF_2)_x$—O—$(CF_2$—$CF_2)_y$—, or —$C_6F_4$—.

Other suitable Brönsted acid compounds will be apparent to those of ordinary skill in the art and are to be considered within the scope of the present invention.

Reactive Silane Connector

The reactive silane connector can comprise between one and twenty carbon atoms. The reactive silane connector contains a silicon atom and at least one leaving group attached to the silicon atom that connects the Brönsted acid compound to the mesoporous silicate to produce the mesoporous catalyst. The reactive silane connector can include compounds that are capable of forming at least one stable MP—O—Si linkage; or alternatively, between one and three MP—O—Si linkages. Upon reaction with the mesoporous catalyst, the —Si atom in the reactive silane connector becomes attached to the SiOH group in the mesoporous silicate to form at least one of the MP—O—Si linkages.

The reactive silane connector can comprise a halosilane group or an alkoxysilane group. The halosilane group minimally has at least one halogen silicon bond; or alternatively, from 1 to 3 halogen silicon bonds. In an embodiment, the halosilane can have the general formula of $X_3$—Si—, wherein X is chlorine, bromine, or an alkoxy group. The alkoxysilane group minimally has at least one alkoxy silicon bond; or alternatively, from 1 to 3 alkoxy silicon bonds. In an embodiment, the alkoxysilane can have the general formula of $(R'O)_3$—Si—, wherein R' can be any hydrocarbon group. Suitable alkoxy groups can include methoxy, ethoxy, or propoxy. Other suitable silane connecting groups will be apparent to those of ordinary skill in the art and are to be considered within the scope of the present invention.

Organic Linking Group

As used herein, an "organic linking group" is defined as an organic substituent group, regardless of functional type, having the required free valencies at one or more carbon atom(s) to link the indicated elements. Thus, an organic linking group can contain organic functional group(s) and/or atom(s) other than carbon and hydrogen (i.e. an organic linking group that can comprise functional groups and/or atoms in addition to carbon and hydrogen). For example, non-limiting examples of atoms other than carbon and hydrogen include halogens, oxygen, nitrogen, and phosphorus, among others. Non-limiting examples of functional groups include ethers, sulfides, amines, and phosphines, among others. Included in the organic linking group definition are heteroatom containing rings, heteroatom containing ring systems, heteroaromatic rings, and heteroaromatic ring systems. Finally, it should be noted that the organic linking group definition includes the organic linking group consisting of inert functional groups, and the hydrocarbon linking group as members. Similarly, an "organylene group" refers to an organic substituent group, regardless of functional type, formed by removing two hydrogen atoms from one or two carbon atoms of an organic compound and an "organic linking group" refers to a generalized organic substituent group formed by removing one or more hydrogen atoms from one or more carbon atoms of an organic compound.

As used herein, an "alkylene group" is defined as a univalent group formed by removing two hydrogen atoms from a hydrocarbon (i.e. a group containing only carbon and hydrogen). An alkylene group can include the term "alkylene" or "hydrocarbylene group." An alkylene group can include rings, ring systems, aromatic rings, and aromatic ring systems that contain only carbon and hydrogen.

In an aspect, the organic linking group can be aromatic group, a fluoroaromatic group, an alkylene group, a fluoroalkylene group, a poly(etherfluoroalkyl) group, or combinations thereof. When the Brönsted acid group contains a sulfonic acid group, the organic linking group generally comprises an alkylene group or an aromatic group. When the Brönsted acid group contains a carboxylic acid group, the organic linking group generally comprises a fluoroalkylene group or a fluoroaromatic group.

In some aspects, when the organic linking group comprises the alkylene group, the alkylene group comprises one to ten carbon atoms; or alternatively, one to five carbon atoms. The alkylene group can be a methylene group, an ethylene group, or a propylene group.

In some embodiments, the organic linking group has the following formula: —$(CH_2)_x$—, wherein x is in a range of one to ten. Alternatively, x can range from one to five.

The organic linking group can be an aromatic group or a fluoroaromatic group. When the organic linking group comprises the aromatic group, the organic linking group has the following formula: —$C_6H_4$—. When the organic linking group comprises the fluoroaromatic group, the organic linking group has the following formula: —$C_6F_4$—, such as tetrafluorobenzene.

The organic linking group can comprise a fluoroalkane group or a fluoroaromatic group. When the organic linking group comprises the fluoroalkane group, the fluoroalkane group generally has the following formula: —$(CF_2$—$CF_2)x$—.

Other suitable organic linking groups will be apparent to those of ordinary skill in the art and are to be considered within the scope of the present invention.

Brönsted Acid Group

In an aspect, the Brönsted acid group is a sulfonic acid group or a carboxylic acid group. In an aspect, the Brönsted acid group comprises a sulfonic acid group. In an aspect, the Brönsted acid group comprises a carboxylic acid group.

In some aspects, the sulfonic acid group has the general formula of —$SO_3H$. In some aspects, the carboxylic acid group has the general formula of —COOH.

Other suitable Brönsted acid groups will be apparent to those of ordinary skill in the art and are to be considered within the scope of the present invention.

Combined Reactive silane connector and Organic Linking Group

Suitable compounds that can be reacted with the mesoporous silicate to form the mesoporous catalyst following subsequent reactions, as described herein, can include phenyltrichlorosilane, phenyltriethoxysilane, phenyltrimethoxysilane, vinyltriethoxysilane, vinyltrimethoxysilane, trichlorovinylsilane, allyltrichlorosilane, or combinations thereof. Other suitable combined silane connecting and organic linking groups will be apparent to those of ordinary skill in the art and are to be considered within the scope of the present invention.

EXAMPLES

Phenolation of Silicate Having Mesoporous Pore Diameters

50 grams of a mesoporous silicate having mesoporous pore diameters was stirred into 250 cc of a 4:1 ethanol:water mixture, along with 10 drops of acetic acid or propionic acid as an acid hydrolysis catalyst. A sufficient amount of phenyl silane (MW 240) to provide a monolayer coating on the surface of the silicate was added while being vigorously stirred at 60-80° C. overnight.

The amount of phenyl silane was doubled and quadrupled to see if additional layers would provide higher amounts of surface phenyl groups. The additional amounts of phenyl silane resulted in higher amounts of surface phenyl groups. The amount of surface phenyl groups was determined later by titration after the surface of the silicate had been sulfonated. Phenyl sulfonated pores of silicate with 0.05 to 0.81 m moles acid per gram of silicate were produced.

Sulfonation of Phenyl Silicate

The silicate structures were dried to constant weight under vacuum to avoid allowing the moisture to dilute and weaken the $SO_3$, which can result in a lower degree of sulfonation. The sulfonation of the phenyl groups attached on the silicate was completed by adding 50 wt. % excess fuming sulfuric acid (containing 18 to 30 wt. % $SO_3$) into 50 grams of vacuum dried phenyl silicate in 300 cc methylene chloride while vigorous stirring at 35° C. for 4 hours. The molar equivalent acids on the surface were determined by acid-base titration.

Because trialkoxy silane is trifunctional and could polymerize on the silica surface to produce a crosslinked multilayer coating instead of a monolayer coating, the surface was silylated with an excessive mono functional silane, phenyldimethyl chlorosilane, which provides only single bonding to the silica surface to check the active silanol sites on the solid surface. Using the mono functional silane produced 0.1 m mole/g of acid after sulfonation, which is the molar equivalent of silanol Si—OH density on the surface. Any loading of phenyl groups significantly above that was due to the crosslinking of the trifunctional phenyl silane to form a multilayer coating thicker than the monolayer coating on the mesoporous catalyst surface. The excess acid functionality could be measured by acid base titrations to show a higher acid concentration. The results can be found in Table 1.

TABLE 1

| Sample No. | Theoretical Sulfonated Phenylsilane, m Mole | Titration Data Molar Equivalents Acid |
|---|---|---|
| 1 | 0.34 | 0.430 |
| 2 | 0.50 | 0.041 |
| 3 | 0.25 | 0.033 |
| 4 | 0.25 | 0.051 |
| 5 | 0.25 | 0.033 |
| 6 | 0.25 | 0.101 |
| 7 | 0.50 | 0.117 |
| 8 | 0.75 | 0.140 |
| 9 | 0.25 | 0.164 |
| 10 | 0.50 | 0.230 |
| 11 | 0.75 | 0.809 |
| 12 | Excess dimethylchlorophenyl silane | 0.106 |
| 13 | 0.50 | 0.037 |
| 14 | 0.50 | 0.247 |
| 15 | 0.50 | 0.272 |
| 16 | | 0.227 |
| 17 | | 0.090 |

While the compositions and methods of this invention have been described in terms of particular embodiments, it will be apparent to those of ordinary skill in the art that variations can be applied to the compositions and methods and in the steps or in the sequence of steps of the methods described herein without departing from the concept, spirit and scope of the invention. For example, it will be apparent that certain agents that are chemically related can be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A mesoporous catalyst having a surface that has been grafted with a substance comprising a Brönsted acid compound, the Brönsted acid compound comprising a reactive silane connector, an organic linking group, and a Brönsted acid group.

2. The mesoporous catalyst of claim 1, wherein the reactive silane connector comprises a halosilane group, an alkoxysilane group, or combinations thereof.

3. The mesoporous catalyst of claim 1, wherein the organic linking group comprises an aromatic group, a fluoroaromatic group, an alkylene group, a fluoroalkylene group, a poly(etherfluoroalkyl) group, or combinations thereof.

4. The mesoporous catalyst of claim 1, wherein the Brönsted acid group comprises a sulfonic acid group, a carboxylic acid group, or combinations thereof.

5. The mesoporous catalyst of claim 1, wherein the mesoporous catalyst has an average pore diameter ranging from about 12 Å to about 100 Å.

6. The mesoporous catalyst of claim 1, wherein the mesoporous catalyst has a surface area ranging from about 400 $m^2/g$ to about 1400 $m^2/g$.

7. The mesoporous catalyst of claim 1, wherein the mesoporous catalyst has a pore volume ranging from about 0.5 cc/g to about 2.0 cc/g.

8. The mesoporous catalyst of claim 1, wherein the mesoporous catalyst has a structure as follows:

MP—O—Si-L-BA, wherein MP comprises a mesoporous silicate, O is oxygen, Si is silicon, L is —$(CH_2)_x$—, —$C_6H_4$—, —$(CF_2—CF_2)_x$—, or —$C_6F_4$— wherein x ranges from 1 to 5, and BA is a sulfonic acid group, and wherein the mesoporous catalyst has an average pore diameter in a range of about 12 Å to about 100 Å, has a surface area ranging from about 400 $m^2/g$ to about 1400 $m^2/g$ and has a pore volume ranging from about 0.5 cc/gram to about 2.0 cc/gram.

9. The mesoporous catalyst of claim 5, wherein the linking group is —$(CF_2—CF_2)_x$— or —$C_6F_4$ and x ranges from 1 to 10.

10. The mesoporous catalyst of claim 9, wherein the Brönsted acid group is carboxylic acid group.

11. The mesoporous catalyst of claim 1, wherein the mesoporous catalyst has a structure as follows:

MP—O—Si-L-BA, wherein MP comprises a mesoporous silicate, O is oxygen, Si is silicon, L is —$(CF_2—CF_2)_x$— or —$C_6F_4$ and x ranges from 1 to 5, and the BA is carboxylic acid group, and wherein the mesoporous catalyst has an average pore diameter in a range of about 12 Å to about 100 Å, has a surface area ranging from about 400 $m^2/g$ to about 1400 $m^2/g$ and has a pore volume ranging from about 0.5 cc/gram to about 2.0 cc/gram.

12. The mesoporous catalyst of claim 2, wherein the organic linking group comprises an aromatic group, a fluoroaromatic group, an alkylene group, a fluoroalkylene group, a poly(etherfluoroalkyl) group, or combinations thereof.

13. The mesoporous catalyst of claim 2, wherein the Brönsted acid group comprises a sulfonic acid group, a carboxylic acid group, or combinations thereof.

14. The mesoporous catalyst of claim 3, wherein the Brönsted acid group comprises a sulfonic acid group, a carboxylic acid group, or combinations thereof.

15. The mesoporous catalyst of claim 12, wherein the Brönsted acid group comprises a sulfonic acid group, a carboxylic acid group, or combinations thereof.

16. A mesoporous catalyst having a structure as follows:

MP—O—Si-L-BA, wherein MP comprises a mesoporous silicate, is oxygen, Si is silicon, L comprises an organic linking group, and BA comprises the Brönsted acid group, and wherein the surface of the mesoporous silicate has been grafted with the —O—Si-L-BA group.

17. The mesoporous catalyst of claim 16, wherein L is an aromatic group, a fluoroaromatic group, an alkylene group, a fluoroalkylene group, a poly(etherfluoroalkyl) group, or combinations thereof.

18. The mesoporous catalyst of claim 16, wherein the Brönsted acid group is sulfonic acid group or a carboxylic acid group.

19. The mesoporous catalyst of claim 16, wherein L is —(CH$_2$)$_x$—, —C$_6$H$_4$—, —(CF$_2$—CF$_2$)$_x$—, or —C$_6$F$_4$— wherein x ranges from 1 to 10.

20. The mesoporous catalyst of claim 19, wherein the Brönsted acid group is a sulfonic acid group.

* * * * *